(12) United States Patent
McIvor et al.

(10) Patent No.: US 6,379,346 B1
(45) Date of Patent: Apr. 30, 2002

(54) INTRODUCER SYSTEM

(75) Inventors: Michael E. McIvor, St. Petersburg, FL (US); Kenneth C. Gardeski, Plymouth; Pedro A. Meregotte, Coon Rapids, both of MN (US); Matthew D. Bonner, Plymouth, MN (US); Timothy G. Laske, Shoreview, MN (US); Linda L. Lach, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/552,250

(22) Filed: Apr. 18, 2000

Related U.S. Application Data

(63) Continuation-in-part of application No. 09/392,715, filed on Sep. 9, 1999.
(60) Provisional application No. 60/142,662, filed on Jul. 6, 1999.

(51) Int. Cl.$^7$ ............................................... A61M 25/00
(52) U.S. Cl. ....................................................... 604/524
(58) Field of Search ........................... 604/524, 95, 264, 604/526, 527, 528, 523, 96.01, 101.01, 101.05; 606/191, 192, 193, 194, 195, 196, 197

(56) References Cited

U.S. PATENT DOCUMENTS

| | | | |
|---|---|---|---|
| 2,688,320 A | * | 9/1954 | Czarnocki ................ 123/193.4 |
| 4,136,703 A | | 1/1979 | Wittkampf |
| 4,345,606 A | | 8/1982 | Littleford |
| 5,318,525 A | * | 6/1994 | West et al. .................. 600/585 |
| 5,396,902 A | | 3/1995 | Brennen et al. |
| 5,484,407 A | | 1/1996 | Osypka |
| 5,728,148 A | | 3/1998 | Bostrom et al. |
| 5,755,760 A | | 5/1998 | Maguire et al. |
| 5,795,341 A | * | 8/1998 | Samson ....................... 604/264 |
| 5,820,592 A | * | 10/1998 | Hammerslag ................ 604/528 |
| 5,902,289 A | | 5/1999 | Swartz et al. |
| 6,004,310 A | * | 12/1999 | Bardsley et al. ............. 604/524 |
| 6,280,433 B1 | * | 8/2001 | McIvor ........................ 604/524 |

* cited by examiner

*Primary Examiner*—Teresa Walberg
*Assistant Examiner*—Daniel Robinson
(74) *Attorney, Agent, or Firm*—Girma Wolde-Michael

(57) ABSTRACT

An introducer is structured with an elongated tube having first and second lumens. A molded handle is coupled to the proximal end of the tube with an opening aligned with the first lumen. Further, a wall adjacent the opening of the handle defines a slot and is located diametrically opposite the second lumen. A tubular reinforcement member is located within the second lumen and the handle is provided with a second opening, thereby having a communication with the second lumen. In another embodiment a lead/catheter introducer includes an implantable lead or catheter having an elongated first lumen through which the lead or catheter passes and a second lumen extends parallel to the first lumen along at least a distal portion thereof. A tubular reinforcement member is disposed within the second lumen. The tubular reinforcement member further includes an internal lumen and a curvable stylet disposed in the lumen.

23 Claims, 8 Drawing Sheets

INTRODUCER SYSTEM

This Application is a Continuation in Part of 09/392,715 filed Sep. 9, 1999 which claims the benefit of Provisional Application 60/142,662 filed Jul. 6, 1999.

BACKGROUND OF THE INVENTION

The present invention relates generally to indwelling catheters and electrode leads and more particularly to introducer systems for introducing catheters and electrode leads into a desired portion of a patient's body.

Catheters and leads are typically placed in a desired location in a patient's body, particularly within the patient's vasculature, by means of introducer systems. These introducer systems typically include an elongated sheath which is inserted into the blood vessel or other portion of the patient's body, through which sheath the catheter or lead is introduced. In those circumstances in which the lead or catheter is to remain in the patient's body for a considerable period of time, it is desirable to be able to remove the introducer sheath over connectors or fittings on the leads or catheters, which may have diameters greater than the inner diameter of the introducer sheath.

In many circumstances, it is also desirable that a hemostasis valve be provided at the proximal end of the introducer sheath, allowing the introducer to be sealed around the lead or catheter body. The presence of the hemostasis valve, which typically includes a rigid housing containing a compressible seal which engages the circumference of the lead body, can pose a problem with regard to removal of the introducer sheath. One mechanism for including a hemostasis valve in a removable sheath is described in co-pending, commonly assigned U.S. patent application Ser. No. 09/116,628, filed Jul. 16, 1998 by Gardeski et al., incorporated herein by reference in its entirety. In the introducer disclosed in the Gardeski et al. application, the introducer sheath is provided with a luer hub on its proximal end, allowing interconnection both to the removable hemostasis valve and to other devices such as valves, T-fittings and the like, using the luer hub. The luer hub is specifically adapted to be slit using a conventional catheter slitter, which may also be employed to slit the introducer sheath.

In order to facilitate location of a catheter or lead in a specific location, it is common to provide a bend or bends in the introducer. The bend may be pre-formed as in U.S. Pat. No. 5,902,289, issued to Swartz. Alternatively, the introducer may be provided with a deflection mechanism allowing it to assume a desired bend or bends while within the vascular system of the patient, as in U.S. Pat. No. 5,484,407, issued to Osypka. Typically, introducers provided with deflection mechanisms are not adapted for removal over connectors or fittings having diameters greater than the inner diameter of the introducer sheath.

SUMMARY OF THE INVENTION

The present invention is directed to providing an introducer or guide catheter which may be employed to direct a lead or catheter to the desired location within the patient's body. In a preferred embodiment, the invention is directed to providing an introducer or catheter having a controllable adjustable curvature in order to facilitate placement of the lead or catheter at specific desired locations in the patient's body, which is adapted to be employed in conjunction with the implant of a permanently indwelling catheter or lead having a connector or fitting at its proximal end which has a diameter greater than the internal diameter of the lumen of the introducer sheath through which the catheter or lead is introduced. In the context of a preferred embodiment of the present invention, these objectives are accomplished by providing an introducer sheath which comprises a two lumen tube, one lumen configured to receive the lead or catheter to be introduced, the second lumen configured to receive an insertable elongated guiding member such as a stylet, which is either shapable or deflectable and which depending upon its configuration, correspondingly alters the configuration of the introducer. In order that the introducer may be reconfigured while in the patient's body, the second lumen is provided with an internal coil or other tubular reinforcement member, allowing for insertion and removal of pre-curved stylet or other elongated guiding member while the introducer is in the patient's body without the risk of perforation of the wall of the second lumen. In order to facilitate removal of the introducer over a lead or catheter having the connector or fitting at its proximal end which is greater than the internal diameter of the first lumen, the introducer is adapted to be slit or split along its length. In some embodiments of the invention, the catheter may be rendered splittable by provision of a weakened zone along its length, for example as described in U.S. Pat. No. 4,354,606, issued to Littleford and incorporated herein in its entirety. In a particularly desirable embodiment, the introducer is provided with a luer lock at its proximal end, facilitating connection of the introducer to a hemostasis valve, t-fitting, or the like. In this particular embodiment, the luer fitting is preferably configured to be slittable by means of a catheter slitter, and is provided with a defined weakened zone along which the luer fitting is adapted to be slit. The weakened zone of the luer lock is preferably aligned with an portion of the external wall of the first lumen of the introducer sheath located diametrically opposite the second lumen.

DETAILED DESCRIPTION OF THE EMBODIMENT

Figure 1:
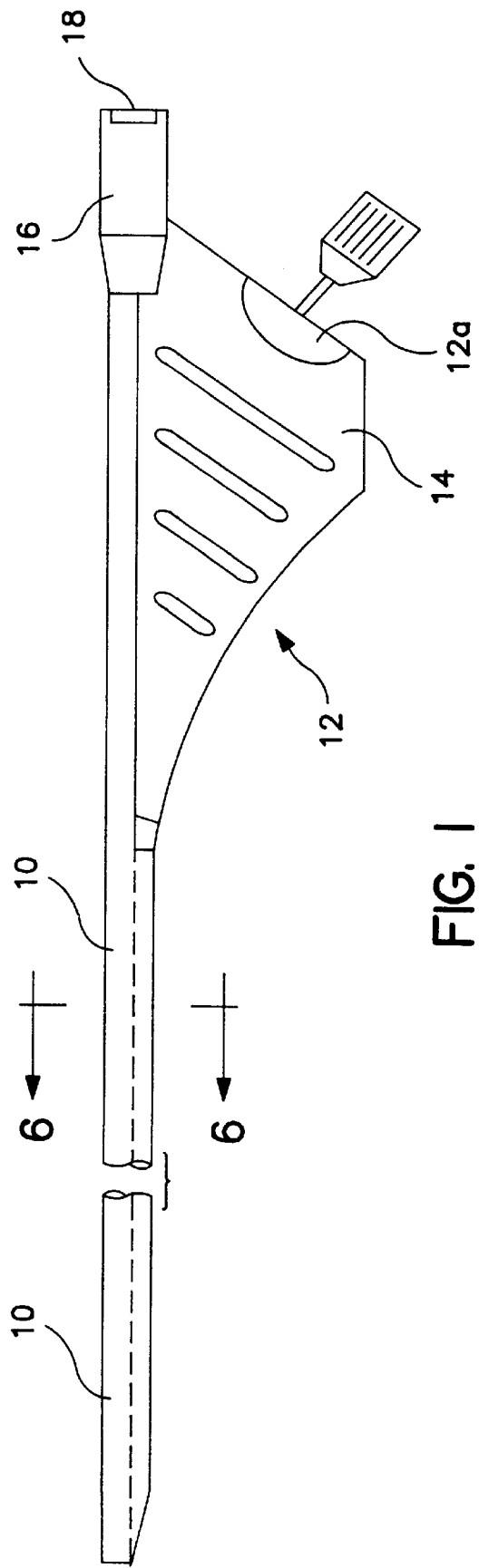
FIG. 1 is a plan view of an introducer according to the present invention.

FIG. 1 is a plan view of an introducer according to the present invention. The introducer is provided with an elongated sheath body 10 which carries a handle 12 which includes a slittable luer fitting 16, molded in its distal end. Handle 12 may be fabricated of multiple components, or is more preferably molded as a single piece part, molded or adhesively bonded to the proximal end of the sheath body 10. Slittable luer hub 16 comprises a hollow, generally conical member which carries laterally extending flanges 18 which engage into the internal threading of a corresponding luer fitting, located in a hemostasis valve, T-fitting or other apparatus to be attached to the sheath. The slittable portion of luer fitting 16, located along the top edge of the fitting is thin enough that it may be readily split using a conventional slitter of the type employed in conjunction with lead introducers, for example, as disclosed in the Gardeski et al. application cited above. The luer fitting 16 must also be sufficiently compliant that when slit, the cut edges may be spread far enough apart to permit passage of the introduced lead or catheter therebetween. The handle 12 allows the physician to pull the sheath against the slitter, during removal of the sheath.

The sheath body 10 of the introducer is provided with two lumens 100 and 102. Lumen 100 is sized to receive the body of the lead or catheter to be introduced and therethrough. Lumen 102 carries an internal reinforcement coil 104 which may be a monofilar or multifilar coil of stainless steel, MP35N, or other biocompatible metal alloy. Lumen 102 terminates distal to lumen 100, within handle 12, while coil 104 extends proximally within handle 12 within a curved internal lumen 110. Conical member 106, adapted to receive stylet 112 or other elongated guiding member, is located at the proximal end of lumen 110. The proximal end of coil 104 is mounted around the distal end of conical member 106, and the lumen defined within coil 104 is aligned with the corresponding internal lumen through conical member 106, through which the stylet 112 passes.

Handle 12 may be molded to sheath body 10 or may be attached by means of adhesive. If adhesive is employed, it may be backfilled in cavity 114, adjacent the proximal termination of lumen 102, and may also be backfilled within lumen 110, if desired. Lumen 100 is longitudinally aligned with the internal lumen 116 through luer fitting 16. A slot 108 extends along the top edge of luer fitting 16. The wall 118 of luer fitting 16 in the vicinity of the slot is thin enough to allow for slitting by means of a conventional catheter slitter, as described above. For example, handle 12 may be molded of polyether block amide plastic, and the thickness of wall 118, may be, for example, 0.010 inches. Sheath body may also be molded of polyether block amide plastic, having an internal lumen 100 sized to receive the catheter or lead intended to be introduced through the lumen, and having a second lumen 102 which may be, for example, 0.030 inches in diameter, sized to receive a coil 104 having a 0.026 inch outer diameter and a 0.018 inch inner lumen diameter adapted to receive stylets having an outer diameter of 0.016 inches.

In use, stylet 112 may be inserted into the lumen 102 before or after insertion of the introducer into the patient's body, and may be provided with a physician selected curvature, in order to induce a corresponding curvature in the body of the introducer sheath 10. For example, the introducer may have a straight stylet introduced into lumen 102 to facilitate advancement of the sheath through the vascular system to a point within the superior vena cava, the straight stylet may thereafter be removed and replaced with a stylet having a physician selected curve adjacent its distal end. The curved stylet may then be passed through lumen 102 to the distal end of the sheath body 10, prevented from perforating the wall of lumen 102 during its passage by coil 104. The introducer may then be advanced into the right atrium, for example, and the distal end of the introducer positioned adjacent the ostium of the coronary sinus, facilitating introduction of a lead located within lumen 100 into the coronary sinus. As an alternative, deflectable stylets or other deflectable elongated guiding members as disclosed in U.S. Pat. No. 5,396,902, issued to Brennen et al., U.S. Pat. No. 5,728,148, issued to Bostrom et al. or U.S. Pat. No. 4,136,703, issued to Wittkampf, all incorporated herein by reference in their entireties, may also be employed in conjunction with the sheath. During insertion, the lead inserted within lumen 100 may be present during advancement of the introducer to the desired site for location of the lead or may be inserted into the introducer thereafter. In either case, a hemostasis valve, mounted to the luer fitting 16 at the proximal end of handle 12 may be employed to prevent leakage of blood through lumen 100.

Figure 3:
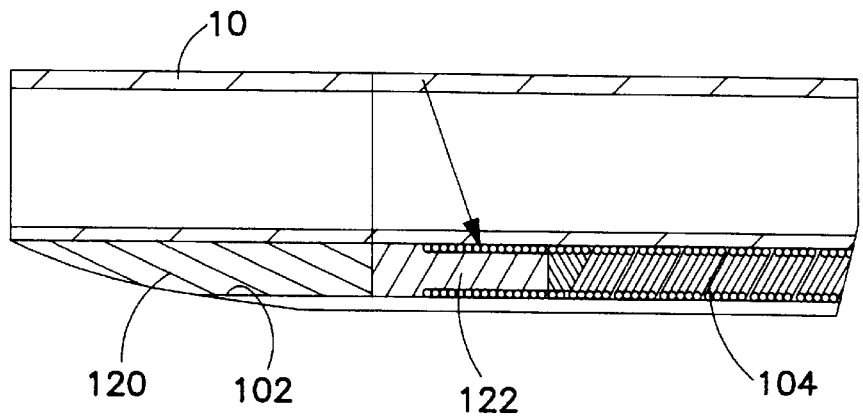
FIG. 3 is an enlarged sectional view through the distal end of the introducer of FIG. 1.

FIG. 3 illustrates a sectional view through the distal tip portion of the introducer sheath body 10. In this view it can be seen that the distal end of lumen 102 is plugged by means of a plastic rod 120, fabricated of a biocompatible plastic. The distal end of coil 104 is crimped or welded to a platinum-iridium core 122, which in turn is bonded within lumen 102 by heat reflow in order to stabilize the distal tip of the coil within sheath body 10. Core 122 also serves to provide a point against which the distal end of the stylet can bear, to assist in advancement of the sheath body 10 through the patient's vascular system. In alternative embodiments, rod 120 may be eliminated and core 122 may be omitted or replaced with a tubular member, additionally allowing the use of a guidewire or other elongated reinforcement member which may extend distal to the sheath body 10.

Figure 4:
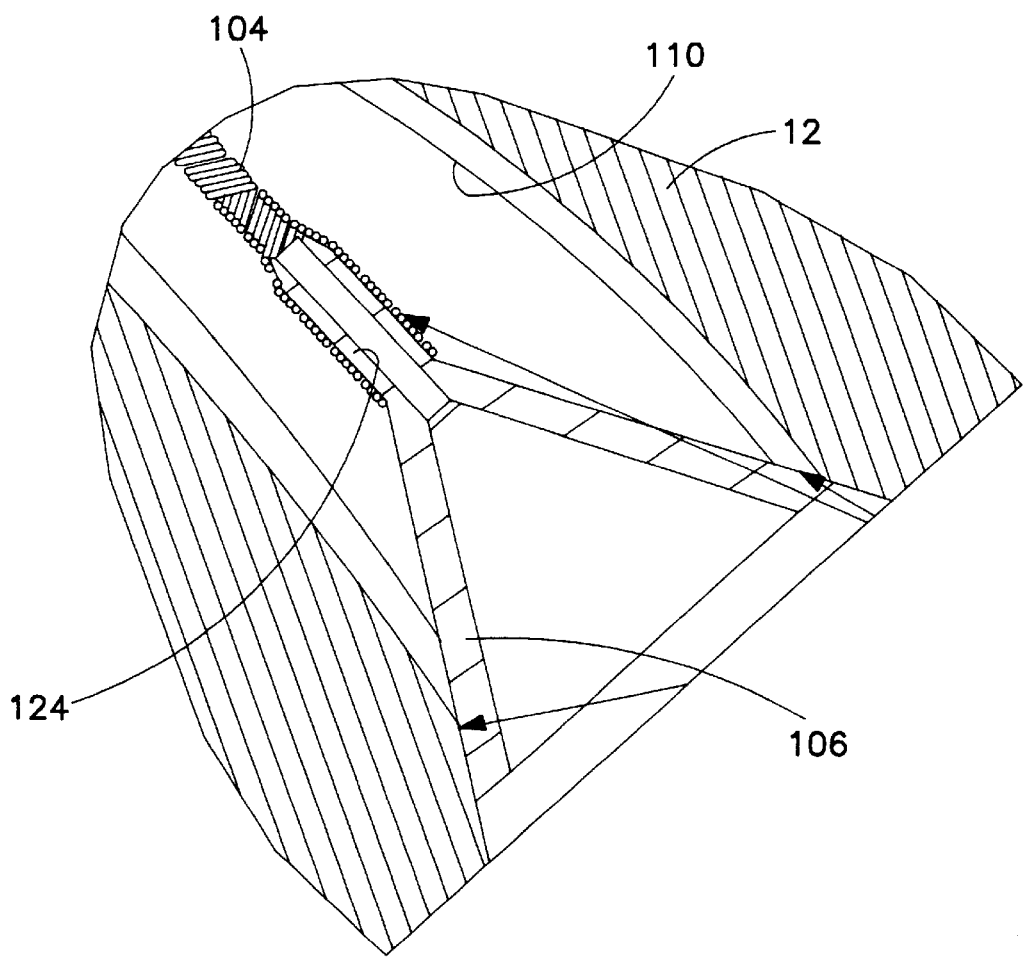
FIG. 4 is an enlarged sectional view through a portion of the proximal end of the introducer of FIG. 1, illustrating the region in which the associated stylet may be inserted.

FIG. 4 is a sectional view through a portion of handle 12, illustrating the interconnection of the coil 104 and the plastic conical member 106. In this view it can be seen that the conical member 106 is provided with a generally tubular extension 124, around which the proximal end of coil 104 is mounted. Coil 104 may also be adhesively bonded to the tubular extension 124 of conical member 106. Conical member 106 may be adhesively coupled to the walls of lumen 110, in order to stabilize it within handle 112. The conical member 106 serves to guide the distal tip of the associated stylet into the interior lumen within coil 104.

Figure 5:
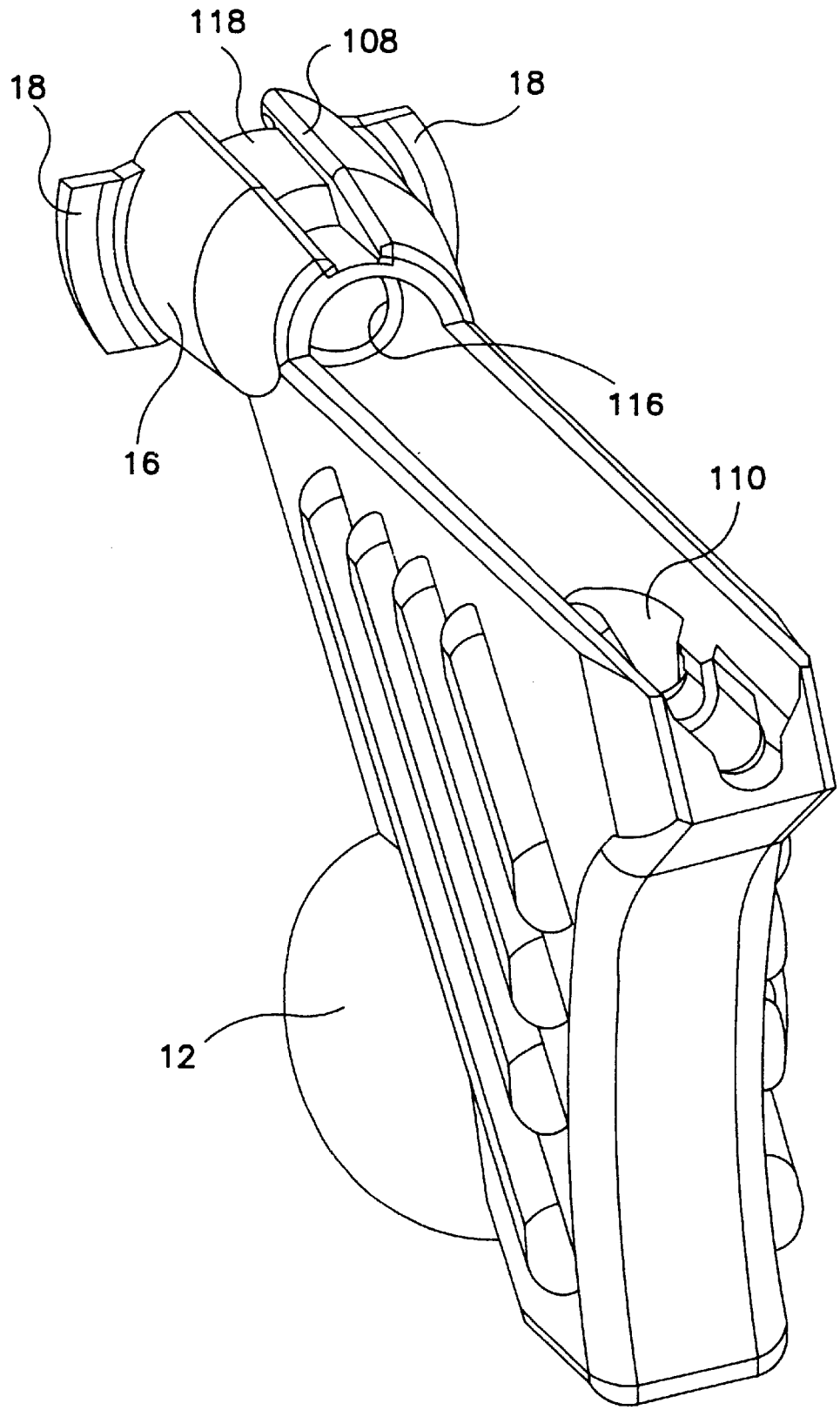
FIG. 5 is a perspective view of the molded handle located at the proximal end of the introducer of FIG. 1, which includes a slittable luer hub.

FIG. 5 is a perspective view of the molded handle 12 of the introducer of FIG. 1. In this view, it can be seen that luer fitting 16 is provided with two laterally extended tabs 18, and the configuration of slot 108, and the relatively thinner wall section 118, adapted to be slit, are both more clearly illustrated. Lumen 116 within the luer fitting 16 and internal lumen 110 within handle 12 are also visible in this view.

Figure 6:
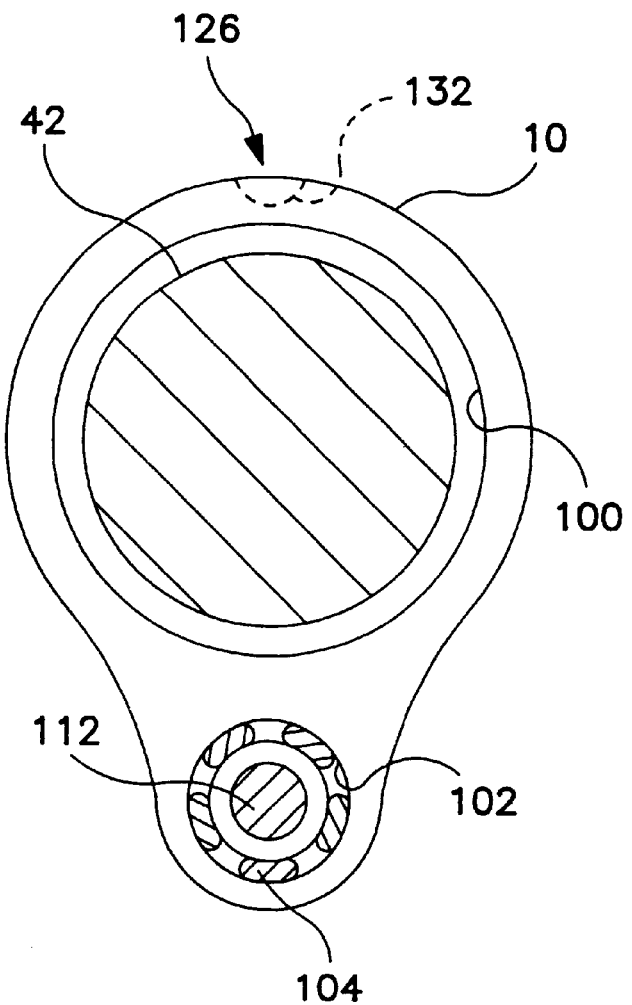
FIG. 6 is a cross sectional view through the sheath of the introducer of FIG. 1.

FIG. 6 is a cross-section through introducer sheath body 10 in a portion distal to the handle 12. In this view, the configuration of the lumens 100 and 102 are visible in cross-section, lumen 100 typically being greater in size than lumen 102. Coil 104, which in this case takes the form of a five filar coil, and stylet 12 are also visible in cross-section within lumen 102. Illustrated schematically at 42 is a body of a lead or catheter to be inserted through lumen 100. It should also be noted that portion 126 of the outer wall of the sheath body 10 surrounding lumen 100, is aligned with the slot 108 (FIG. 5) of the handle 12. Thus, the configuration of handle 12 is adapted to initiate the slitting of sheath 10 at a point diametrically opposite from lumen 102, reducing the possibility that the slitter will inadvertently engage coil 104 during slitting of the wall of sheath body 10. Illustrated in broken outline at 132 is an optional groove 132, located diametrically opposite lumen 102, which may extend along the length of the sheath body 10 and may serve either to facilitate slitting of the sheath body or to render the sheath body splittable in the manner of the Littleford patent cited above.

Figure 7:
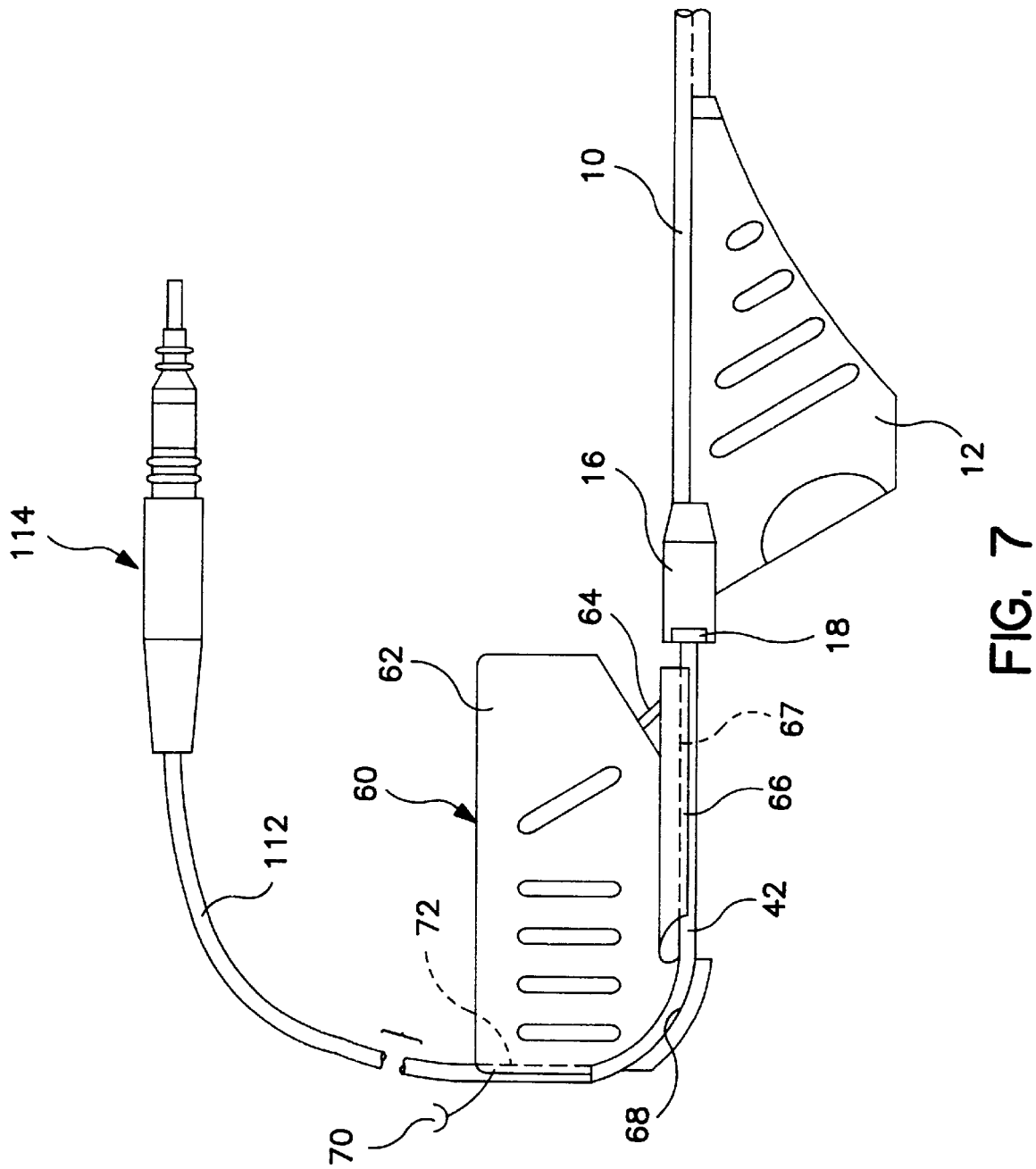
FIG. 7 illustrates the use of a slitter in conjunction with the introducer of FIG. 1.

FIG. 7 illustrates the proximal portion of the introducer of FIG. 1, in conjunction with the body 42 of a lead or catheter inserted therein and an associated slitter 60, prior to removal of the introducer from the body 42 of the lead or catheter. The body 42 of the catheter or lead is inserted through luer fitting 16, and extends distally through introducer sheath 10 to a desired location within the patient's body, for example, the patient's coronary sinus. The lead or catheter should be understood to be properly positioned, so that removal of the introducer is now possible. It should be noted that the stylet has been removed from the introducer, prior to slitting of the introducer.

Figure 2:
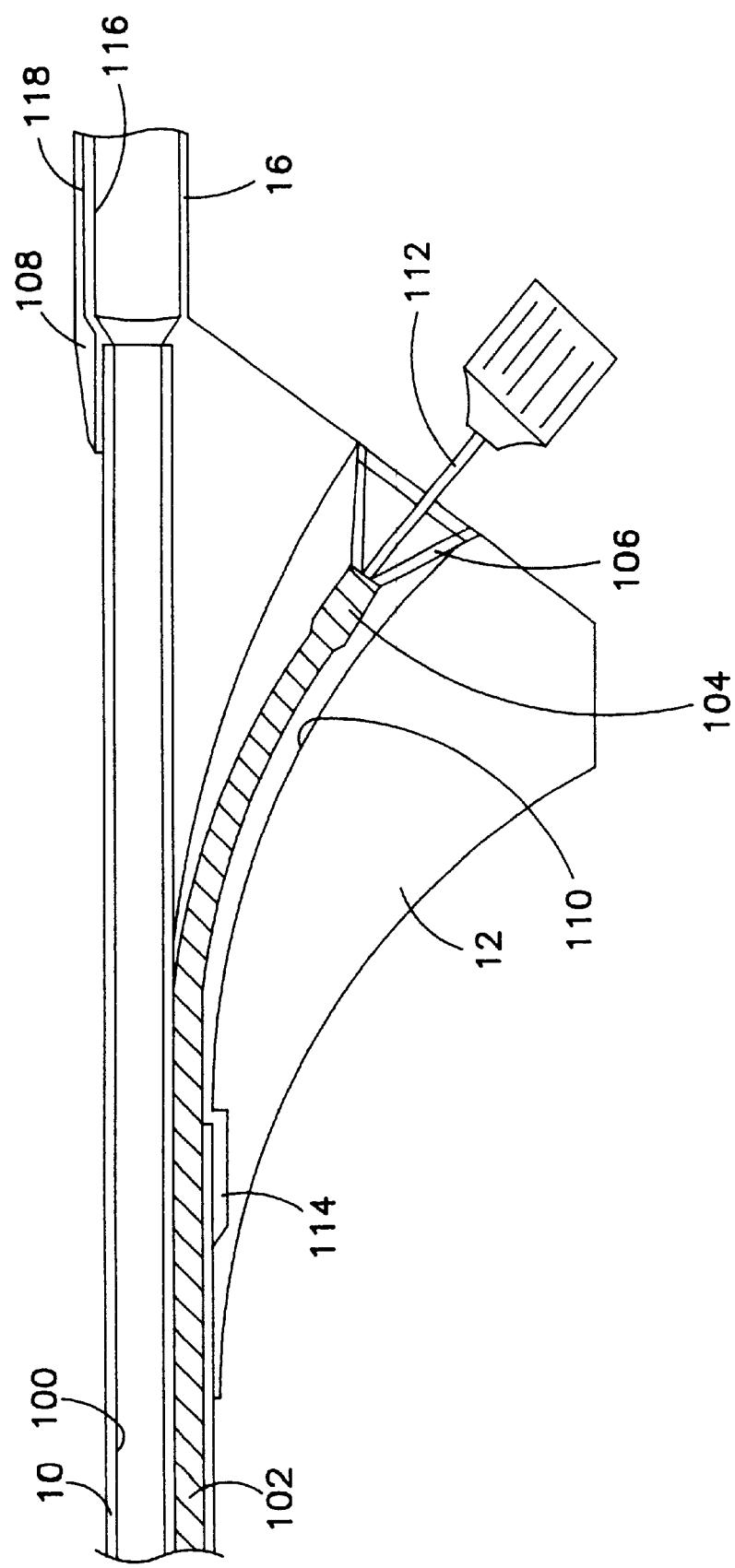
FIG. 2 is an enlarged sectional view through the proximal end of the introducer of FIG. 1.

The slitter illustrated is particularly adapted for use in conjunction with removal of introducer sheaths over leads or catheters, and is described in more detail in the above-cited Gardeski, et al. application, cited above. Slitter 60 is provided with a handle 62 which carries a cutting blade 64, which in turn is aligned with slot 108 (FIG. 5) running along the top edge of luer fitting 16. A generally C-shaped member 66 is provided sized to snap onto and hold the lead or catheter body 42, visible within C-shaped member along broken outline 66. C-shaped member 66 holds the lead in a fixed configuration during proximal movement of the handle 12 and the sheath body 10 along blade 64. Curved groove 68 serves to shield the lead body 42 from the cut edges of the luer fitting 16 and sheath body 10 during removal, preventing damage to lead or catheter body 42. An additional C-shaped groove 70 is provided along the proximal edge of handle 62, also engaging lead or catheter body 42, visible along broken outline 72. At the proximal end of lead or catheter body 42 is a connector assembly 44 which, as illustrated, takes the form of a bipolar IS-1 type connector assembly of a type typically employed with cardiac pacing leads. Alternatively, some other type of electrical or fluid connector might be provided. For purposes of the present invention, it need only be noted that the outer diameter of connector assembly 44 is greater than the internal diameter of lumen 110 (FIG. 2) through sheath body 10.

Because the slot 18 is located diametrically opposite the second lumen and coil 104 (FIG. 2) of the introducer, and because handle 12 extends diametrically opposite from the slot 108 (FIG. 5), the blade 64 of the slitter 60 is naturally directed along a path which tends to prevent it from coming into contact with the coil 104 within lumen 102 of the introducer sheath. In removing the sheath from the lead, the physician simply holds the handle 62 of the slitter in one hand, and with the other hand holding handle 12 directed diametrically opposite handle 62 of the slitter, pulls the introducer proximally over blade 64. The configuration of the slot 108 and handle 12 of the introducer provides a mechanism for the physician to easily maintain the location of the blade 64 along a portion of the wall of the introducer sheath opposite lumen 102, during removal, eliminating complications that might otherwise occur due to engagement of the coil 104 with slitter 64. In the event that a splittable, rather than a slittable luer lock and/or a splittable sheath body is employed, handle 62 and/or stylet may be employed to assist in initiating the splitting process by pulling the stylet and/or the handle downward against the body of the lead 100.

Figure 8:
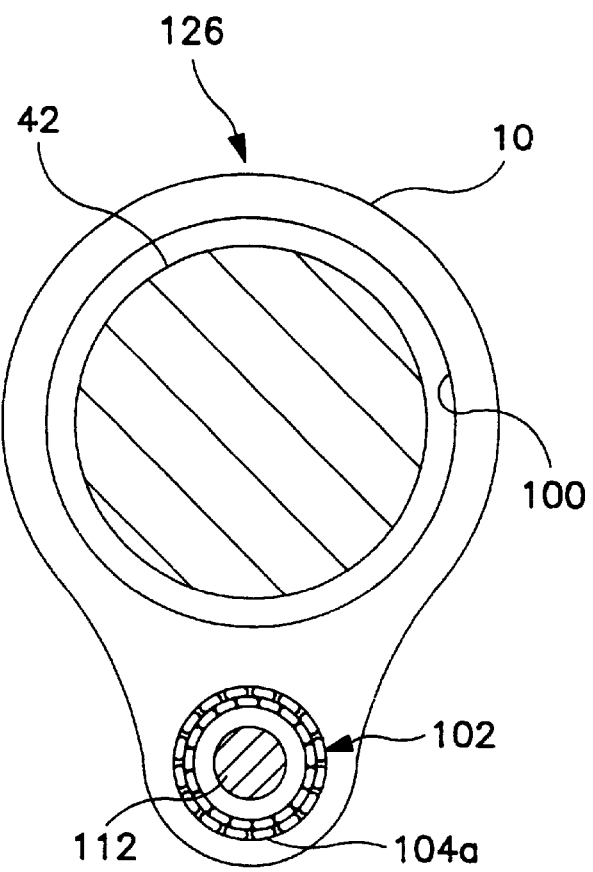
FIG. 8 is a cross sectional view through the sheath of an alternative embodiment of an introducer according to the present invention.
Figure 9:
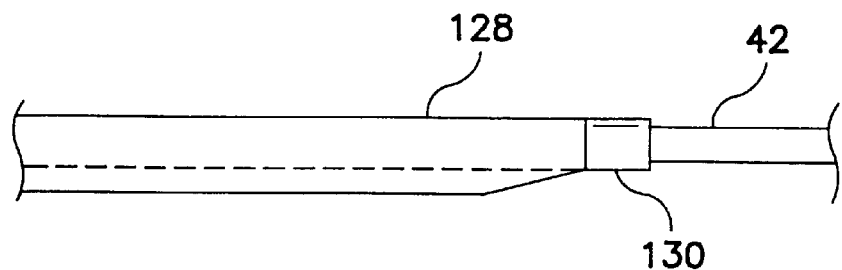
FIG. 9 is a plan view of the distal portion of an additional alternative embodiment of an introducer according to the present invention.

FIG. 8 is a cross-section through an alternative embodiment of an introducer according to the present invention, corresponding to the introducer of FIGS. 1–7 with the exception that the coil 104 has been replaced by a wire braid 104a. All other labeled components correspond to those identically numbered and described in conjunction with FIGS. 1–7 as described above. The cross section is taken through the introducer sheath body 10 in a portion distal to the handle 12 (FIG. 5). Wire braid 104a and stylet 12 are also visible in cross-section within lumen 102. Illustrated schematically at 42 is a body of a lead or catheter to be inserted through lumen 100. It should also be noted that in this embodiment as well, portion 126 of the outer wall of the sheath body 10 surrounding lumen 100, is aligned with the slot 108 (FIG. 5) of the handle 12. Thus, the configuration of handle 12 in this embodiment as well is adapted to initiate the slitting of sheath 10 at a point diametrically opposite from lumen 102, reducing the possibility that the slitter will inadvertently engage coil 104a during slitting of the wall of sheath body 10.

Figure 10:
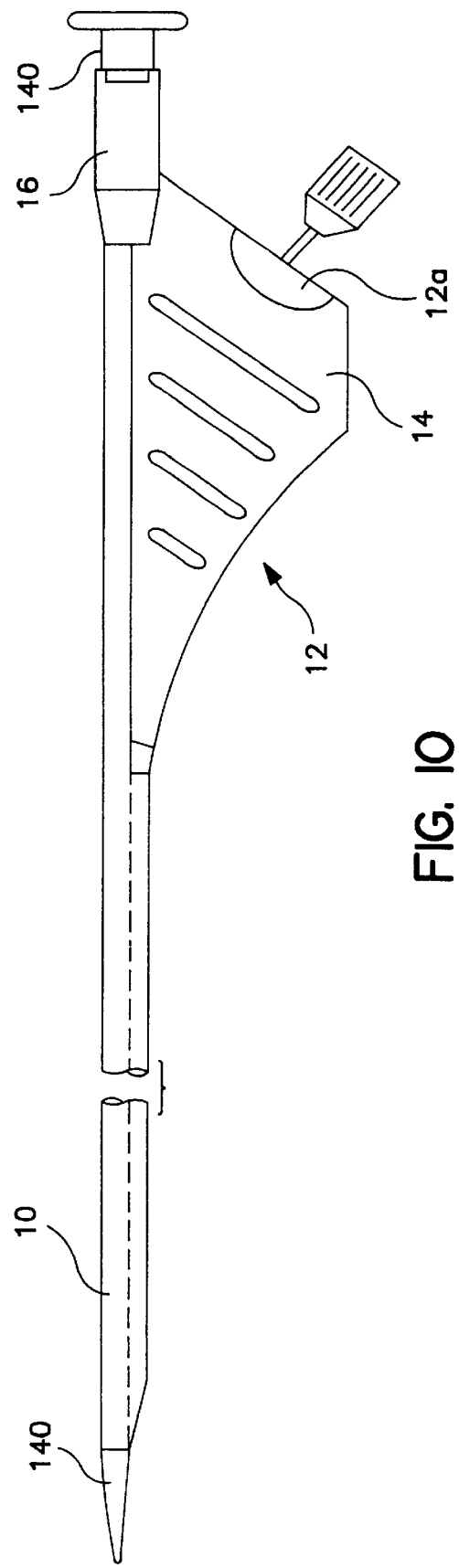
FIG. 10 is a plan view of the distal portion of an introducer according to the present invention, in conjunction with a dilator, located in the first lumen.

FIG. 10 is a plan view of a distal portion of an additional alternative embodiment according to the present invention in which an electrode 130 is mounted to the distal tip of the sheath body 128, which may correspond to either sheath body 10 (FIG. 1) or sheath body 126 (FIG. 8). The electrode is coupled either a metallic coil corresponding to coil 104 (FIG. 2) or to a metallic braid corresponding to braid 104a (FIG. 8), which in turn is coupled to a conventional electrical connector located on a handle at the proximal end of the introducer. The electrode may be employed for mapping the or other purposes, for example as disclosed in conjunction with the electrode bearing introducer catheter described in U.S. Pat. No. 5,755,760, issued to Maguire, et al., incorporated herein by reference in its entirety.

FIG. 10 illustrates the introducer of FIG. 1, with an optional elongated dilator 140 extending through lumen 100 (FIG. 2) and out the distal end of the introducer. Dilator 140 may be employed in conjunction with a guidewire and needle to insert the introducer into a patient's blood vessel, in the manner disclosed in the above-cited Littleford patent.

In conjunction with the above disclosure, we claim:

1. An introducer, comprising:
    an elongated tube having first and second lumens;
    a molded handle coupled to the proximal end of the tube, having a proximal opening aligned with the first lumen of the tube and having a wall adjacent the opening of the handle which defines a slot, located diametrically opposite the second lumen of the tube; and
    a tubular reinforcement member located within the second lumen of the tube, the handle also being provided with a second opening, open to the second lumen of the tube.

2. An introducer according to claim 1 wherein the tubular reinforcement member is a coil.

3. An introducer according to claim 2 wherein the tubular reinforcement member is a metal coil.

4. An introducer according to claim 1 wherein the tubular reinforcement member is a braid.

5. An introducer according to claim 2 wherein the tubular reinforcement member is a metal braid.

6. An introducer according to claim 1 wherein the tubular reinforcement member is a metal member.

7. An introducer according to claim 1 wherein a portion of the handle extends laterally from the tube in a direction diametrically opposite from the slot.

8. An introducer according to claim 7 wherein the second opening of the handle is located in the laterally extending portion of the handle.

9. A lead/catheter introducer system comprising:

an implantable lead or catheter;

an introducer having an elongated first lumen through which the lead or catheter passes and a second lumen, extending parallel to the first lumen along at least a distal portion thereof;

a tubular reinforcement member located within the second lumen of the tube, the tubular reinforcement member in turn having an internal lumen; and a curvable stylet, located in the lumen of the tubular reinforcement member.

10. A system according to claim 9 wherein the tubular reinforcement member is a coil.

11. A system according to claim 10 wherein the tubular reinforcement member is a metal coil.

12. A system according to claim 9 wherein the tubular reinforcement member is a braid.

13. A system according to claim 12 wherein the tubular reinforcement member is a metal braid.

14. A system according to claim 9 wherein the tubular reinforcement member is a metal member.

15. A method of locating a lead or catheter in a desired location within a patient's body, comprising:

inserting the lead or catheter into a first longitudinal lumen of a guide sheath;

inserting a stylet into a second longitudinal lumen of the guide sheath;

advancing the guide sheath, stylet and the catheter or lead to the desired location in the patient's body;

removing the stylet; and removing the guide sheath from the lead or catheter by opening an outer wall of the first lumen along its length and removing the guide sheath from the lead or catheter.

16. A method according to claim 15, wherein the step of opening the wall of the guide sheath comprises slitting the wall.

17. A method according to claim 16, wherein the step of slitting the wall comprises slitting the wall along a portion of the wall located diametrically opposite the second longitudinal lumen.

18. A method of locating a lead or catheter in a desired location within a patient's body, comprising:

inserting the lead or catheter into a first longitudinal lumen of a guide sheath;

inserting a stylet into a second longitudinal lumen of the guide sheath having a tubular reinforcement member located therein;

advancing the guide sheath, stylet and the catheter or lead to the desired location in the patient's body;

removing the stylet; and removing the guide sheath from the lead or catheter by opening an outer wall of the first lumen along its length and removing the guide sheath from the lead or catheter.

19. A method according to claim 18, wherein the step of opening the wall of the guide sheath comprises slitting the wall.

20. A method according to claim 19, wherein the step of slitting the wall comprises slitting the wall along a portion of the wall located diametrically opposite the second longitudinal lumen.

21. A method of locating a lead or catheter in a desired location within a patient's body, comprising:

inserting the lead or catheter into a first longitudinal lumen of a guide sheath;

inserting a stylet into a second longitudinal lumen of the guide sheath having a coiled reinforcement member located therein;

advancing the guide sheath, stylet and the catheter or lead to the desired location in the patient's body;

removing the stylet; and removing the guide sheath from the lead or catheter by opening an outer wall of the first lumen along its length and removing the guide sheath from the lead or catheter.

22. A method according to claim 21, wherein the step of opening the wall of the guide sheath comprises slitting the wall.

23. A method according to claim 21, wherein the step of slitting the wall comprises slitting the wall along a portion of the wall located diametrically opposite the second longitudinal lumen.

* * * * *